US011350702B2

(12) United States Patent
Doenges (10) Patent No.: US 11,350,702 B2
(45) Date of Patent: *Jun. 7, 2022

(54) ARTICLE OF FOOTWEAR

(71) Applicant: Under Armour, Inc., Baltimore, MD (US)

(72) Inventor: Nicole Doenges, Baltimore, MD (US)

(73) Assignee: UNDER ARMOUR, INC., Baltimore, MD (US)

( * ) Notice: Subject to any disclaimer, the term of this patent is extended or adjusted under 35 U.S.C. 154(b) by 233 days.

This patent is subject to a terminal disclaimer.

(21) Appl. No.: 16/595,742

(22) Filed: Oct. 8, 2019

(65) Prior Publication Data

US 2020/0029656 A1 Jan. 30, 2020

Related U.S. Application Data

(63) Continuation of application No. 15/939,401, filed on Mar. 29, 2018, now Pat. No. 10,470,524.

(60) Provisional application No. 62/478,866, filed on Mar. 30, 2017.

(51) Int. Cl.
*A43C 1/04* (2006.01)
*A43C 5/00* (2006.01)

(52) U.S. Cl.
CPC . *A43C 5/00* (2013.01); *A43C 1/04* (2013.01)

(58) Field of Classification Search
CPC .. A43C 1/00; A43C 1/003; A43C 1/06; A43C 1/04; A43C 11/00; A43C 11/004; A43C 11/002

USPC .................................................. 36/58.5, 58.6
See application file for complete search history.

(56) References Cited

U.S. PATENT DOCUMENTS

| 8,020,319 | B1 | | 9/2011 | Mohaupt | |
|---|---|---|---|---|---|
| D715,531 | S | * | 10/2014 | Cochrane | ...................... D2/973 |
| 10,136,701 | B2 | * | 11/2018 | Klein | ...................... A43B 3/126 |
| 10,470,524 | B2 | * | 11/2019 | Doenges | .................. A43C 5/00 |
| 2005/0081403 | A1 | * | 4/2005 | Mathieu | .................. A43C 1/003 |
| | | | | | 36/50.1 |
| 2013/0340283 | A1 | * | 12/2013 | Bell | ...................... A43B 23/025 |
| | | | | | 36/51 |
| 2017/0105486 | A1 | * | 4/2017 | Klein | ...................... A43C 1/06 |
| 2017/0105487 | A1 | * | 4/2017 | Klein | .................. A43B 23/0245 |

* cited by examiner

*Primary Examiner* — Ted Kavanaugh (74) *Attorney, Agent, or Firm* — Edell, Shapiro & Finnan, LLC (57) ABSTRACT

The present invention is directed toward an article of footwear with an improved eyelet system independent of the upper. The article of footwear includes an upper and a sole structure, where the sole structure includes a top surface, a bottom surface, a lateral side and a medial side. The article of footwear further includes an eyelet system coupled to the top surface of the sole structure. The eyelet system includes a base structure and a plurality of looped strand portions coupled to the base structure. The base structure is coupled to the top surface of the sole structure such that the plurality of looped strand portions extend outwardly from the sole structure, enabling the looped strand portions to receive a fastening element.

15 Claims, 5 Drawing Sheets

ARTICLE OF FOOTWEAR

CROSS-REFERENCE TO RELATED APPLICATIONS

This application is a continuation of U.S. application Ser. No. 15/939,401, entitled "Article of Footwear," and filed on Mar. 29, 2018, which claims priority under 35 U.S.C. 119(e) to U.S. Provisional Patent Application Ser. No. 62/478,868, entitled "Article of Footwear with Eyelet System", filed Mar. 30, 2017, the disclosures of which are incorporated herein by reference in their entirety for all purposes.

FIELD OF THE INVENTION

The present invention relates to an article of footwear with an improved eyelet system for configuring a fastening element (e.g., string, laces, etc.) across the article of footwear to provide an improved and custom fit of an upper around a foot.

BACKGROUND OF THE INVENTION

Conventional eyelets of articles of footwear are configured to receive a fastening element (e.g., string, laces, etc.), and are typically formed within the upper proximate to the tongue. These conventional eyelets prevent the upper of the article of footwear from properly contouring and conforming to the various shapes of feet that may be disposed within the article of footwear, reducing the comfort of the article of footwear. In addition, if the eyelets are openings formed in an upper constructed from a knit material/fabric material, the eyelets may be subjected to amounts of stress or a force that causes the upper to rip at the eyelets.

It would be desirable to provide an eyelet system that is constructed from a base structure and a plurality of strands coupled to the base structure in a manner that forms a plurality of eyelet loops, where, when constructing an article of footwear, the base structure may be coupled to the article of footwear at any location. It would be further desirable to provide an article of footwear with eyelets that are flexible and adaptable, where the eyelets and the fastening element operate, move, and contour independent of the upper of the article of footwear. Furthermore, it would be desirable for eyelets that enable the upper of the article of footwear to tightly contour and conform to the shape of any foot placed within the article of footwear.

SUMMARY OF THE INVENTION

The present invention is directed toward an article of footwear with an improved eyelet system. The article of footwear includes an upper and a sole structure, where the sole structure includes a top surface, a bottom surface, a lateral side, and a medial side. The article of footwear further includes an eyelet system coupled to the top surface of the sole structure. The eyelet system includes a base structure and a plurality of looped strand portions coupled to the base structure. In one embodiment, the base structure is coupled to the top surface of the sole structure such that the plurality of looped strand portions extend outwardly from the sole structure, enabling the looped strand portions to receive a fastening element. Coupling the base structure of the eyelet system to the sole structure enables the looped strand portions to conform and contour to the topography of a foot disposed within an article of footwear without pulling or straining the upper in undesirable manners. In other embodiments of the present invention, the eyelet system may be coupled to any location (e.g., sole structure, upper, etc.) of the article of footwear that optimizes comfort, support, and functionality of the eyelets.

In one embodiment, an article of footwear includes an upper, a sole structure, and an eyelet system. The upper may define a cavity. The sole structure may be coupled to the upper. Furthermore, the sole structure may include a top surface and a bottom surface. The eyelet system may include a base structure and a plurality of loop strand portions. The plurality of loop strand portions may extend from the base structure of the eyelet system. The base structure may be coupled to the top surface of the sole structure.

In another embodiment, an article of footwear also includes an upper, a sole structure, and an eyelet system. The upper may define a cavity for receiving a foot of a wearer of the article of footwear. The sole structure may be coupled to the upper. The eyelet system may be coupled to the sole structure. The eyelet system further includes a plurality of loop strands that extend outwardly from between the upper and the sole structure.

In yet another embodiment, an eyelet system for an article of footwear includes a base structure and a plurality of loop strands. The base structure may have a top layer and a bottom layer that is coupled to the top layer. The base structure may further define a first edge and a second edge. The plurality of loop strands may extend from the first edge of the base structure. Furthermore, the plurality of loop strands may extend from between the top layer and the bottom layer. The eyelet system may be configured to be coupled to a sole structure of the article of footwear when the article of footwear is constructed.

The above and still further features and advantages of the present invention will become apparent upon consideration of the following detailed description of specific embodiments thereof.

BRIEF DESCRIPTION OF THE DRAWINGS

Like reference numerals have been used to identify like elements throughout this disclosure.

DETAILED DESCRIPTION OF THE INVENTION

The present invention relates to an article of footwear with a plurality of eyelets formed by looped strand portions being coupled to a base structure, where the base structure may be secured to the article of footwear at a variety of locations when constructing the article of footwear. This enables the looped strand portions that form the eyelets to position on the article of footwear at optimal locations without causing unwanted pulling or stretching of the upper of the article of footwear when the fastening element (e.g., string, laces, etc.) is tightened (i.e., pulled through the eyelets).

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the description herein. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

An article of footwear or shoe 10 includes a lateral side 100 oriented along the lateral or little toe side of the user's foot, a medial side 300 oriented along the medial or big toe side of the user's foot, a toe (i.e., front) end 102 that corresponds with the toes of the user's foot, and a heel (i.e., rear) end 104 that corresponds with the heel of the user's foot. While the example embodiment depicted in the FIGS. 1, 2A, 2B, 3A, and 3B shows an article of footwear 10 configured for a left foot, it is noted that the same or similar features can also be provided for an article of footwear 10 configured for a right foot (where such features of the left footed article of footwear are reflection or "mirror image" symmetrical in relation to a right footed article of footwear).

The article of footwear 10 may include a forefoot region 110 that generally aligns with the ball and toes of a user's foot (i.e., when a user is wearing the article of footwear 10), a midfoot region 112 that generally aligns with the arch and instep areas of the user's foot, and a hindfoot region 114 that generally aligns with the heel and ankle areas of the user's foot. The embodiment of the article of footwear 10 illustrated includes an upper 120 and a sole structure 130. The article of footwear 10 illustrated in FIGS. 1, 2A, 2B, 3A, and 3B may be utilized and applied for use in a running shoe. Other embodiments of the article of footwear 10 illustrated in FIGS. 1, 2A, 2B, 3A, and 3B may be utilized and applied for use in any type of article of footwear, including, but not limited to, shoes, sneakers, boots, sandals, etc.

The upper 120 forms an envelope or pocket that, in cooperation with the sole structure 130, defines a foot cavity operable to house (i.e., cover and protect) the foot of the wearer of the article of footwear 10. The upper 120 may be constructed from various materials that are configured to conform and contour to a foot that is placed within the upper 120 of the article of footwear 10. In some embodiments, the various materials that may be used to construct the upper 120, include, but are not limited to, leather, synthetic leather, rubber, textile fabrics (e.g., breathable fabrics, knit fabrics, woven fabrics, mesh fabrics, synthetic fabrics), etc. One material used for the upper 120 may be configured to have a high degree of stretchability and compressibility, while another material used on the upper 120 may have a lower degree of stretchability and compressibility. The materials used on the upper 120 may be generally lightweight and flexible, and may be configured to provide comfort to the user and provide other desirable features. The materials used on the upper 120 may be configured to have desirable aesthetics and functional features that incorporate durability, flexibility, air permeability and/or other types of desirable properties to the upper 120. In one embodiment, the upper 120 may be formed of a high porosity material operable to permit the flow of fluid (e.g., air) therethrough. In another embodiment, the upper 120 may be formed of a low porosity material.

Figure 1:
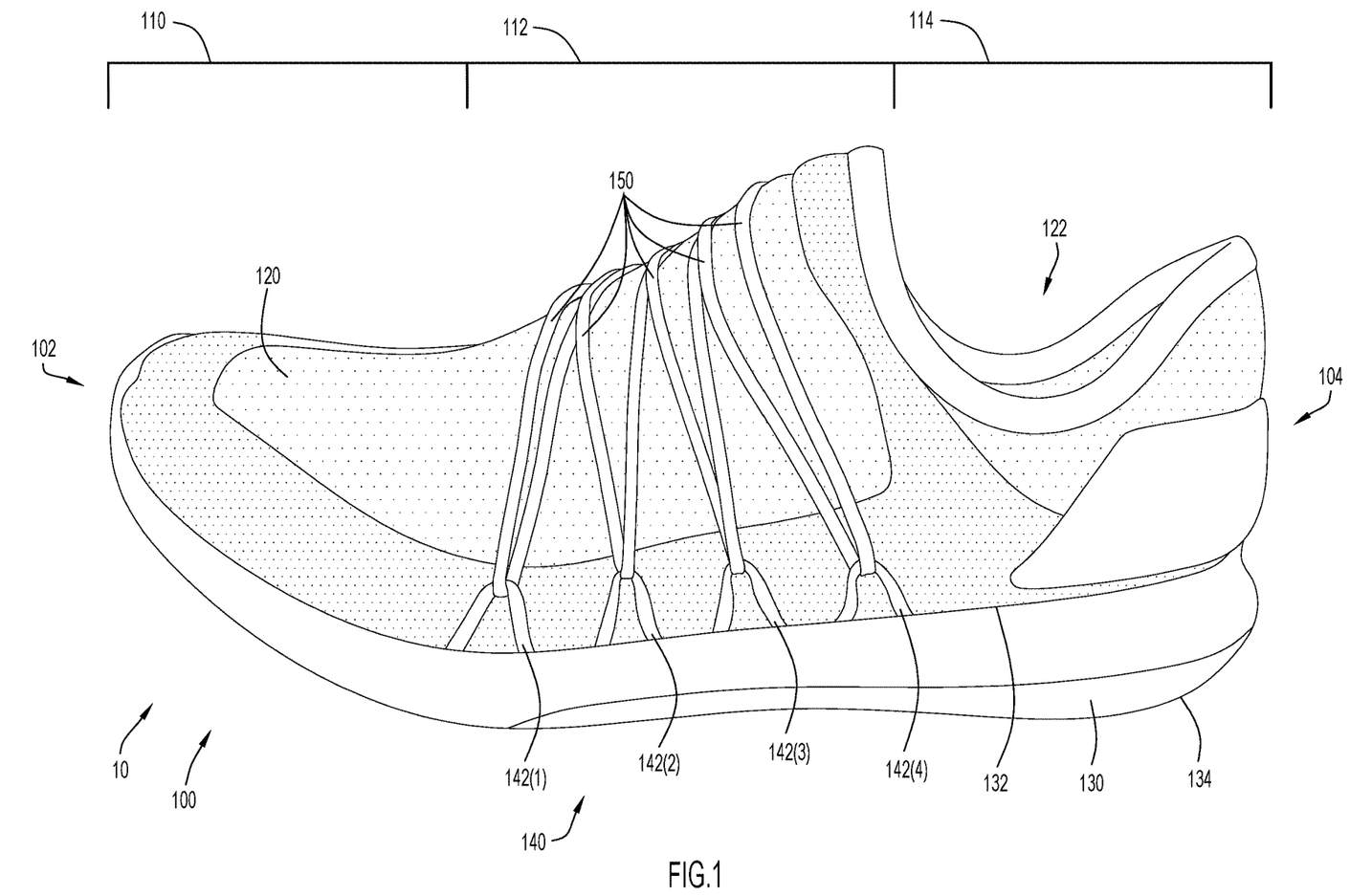
FIG. 1 illustrates a side elevational view of an embodiment of an article of footwear according to the present invention.

In the embodiment illustrated in FIG. 1, the upper 120 is a tongue-less upper that is formed or constructed from a knit material/fabric (e.g., flat knit, circular knit, etc.) or a woven material/fabric. This enables the upper 120 to be more flexible, more elastic, and/or more breathable than uppers constructed of conventional materials (e.g., leather, suede, plastics, etc.). This also enables the upper 120 of the article of footwear 10 to be lighter than conventional footwear. In addition, this upper construction enables the upper 120 to comfortably contour to the shape of a foot disposed within the article of footwear 10. As further illustrated in FIG. 1, a collar or opening 122 may be disposed in the hindfoot region 114 of the upper 120. The opening 122 provides access to the interior of the upper 120 and enables a foot of a wearer of the article of footwear 10 to be placed within the interior of the upper 120.

Figure 3A:
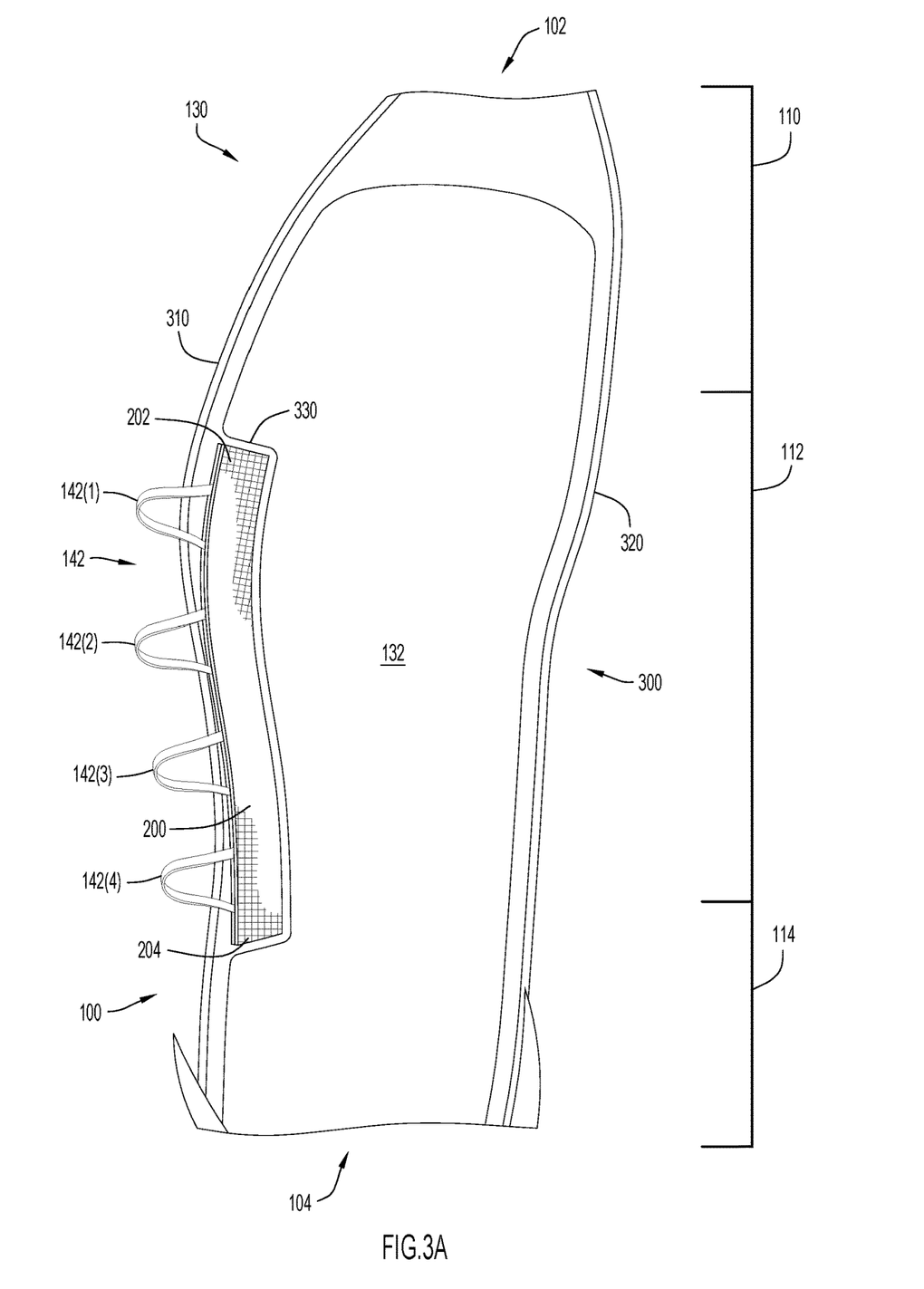
FIG. 3A illustrates a top view of the sole structure of the embodiment of the article of footwear illustrated in FIG. 1.
Figure 3B:
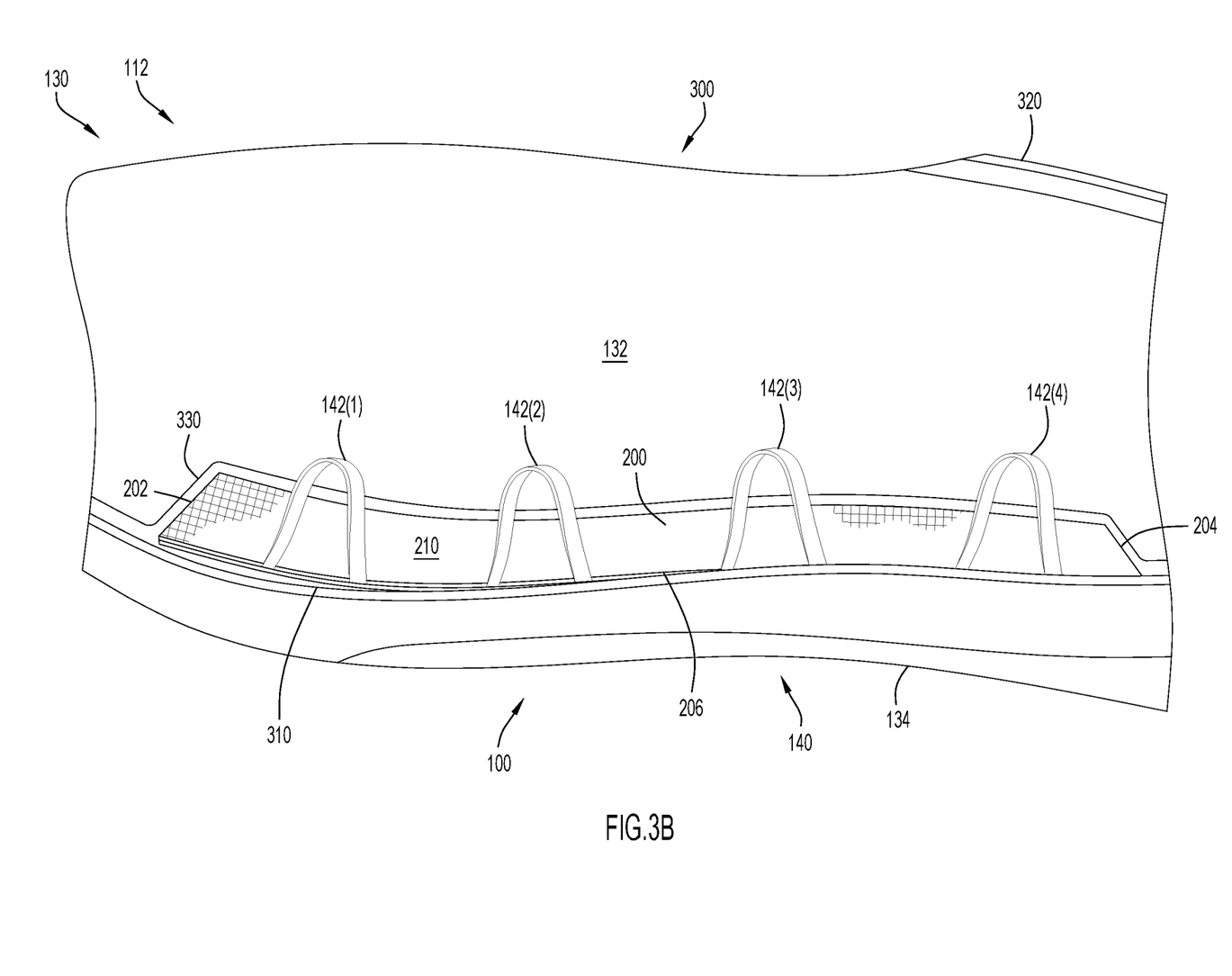
FIG. 3B illustrates a side elevational view of the eyelet system of FIG. 2 adhered to the top surface of the sole structure of FIG. 3A of the embodiment of the article of footwear illustrated in FIG. 1.

As previously explained, the upper 120 is disposed atop a sole structure 130. FIGS. 1, 3A, and 3B further illustrates that the sole structure 130 includes a top surface 132 and a bottom surface 134. The top surface 132 is configured to be coupled to the upper 120 via any conventional and/or other suitable manner (e.g., via any form of adhesion or bonding, via a woven connection, via one or more types of fasteners, etc.). The bottom surface 134 is configured to contact and impact a support surface, while also supporting the article of footwear 10 on the support surface. As best illustrated in FIG. 3A, the sole structure 130 includes a lateral edge 310 disposed along the lateral side 100 of the article of footwear 10, and a medial edge 320 disposed along the medial side 300 of the article of footwear 10. In the particular embodiment depicted, the sole structure 130 may be constructed of a compression material such as ethylene-vinyl acetate (EVA) foam. The compression material is configured to compress on impact and provide cushion to the user's foot as the article of footwear 10 impacts the support surface.

As further detailed below, the article of footwear 10 includes a fastening anchor loop or eyelet system 140. In the embodiment illustrated in FIG. 1, the eyelet system 140 extends outwardly from an area between the coupling of the upper 120 to the top surface 132 of the sole structure 130. The eyelet system 140 includes a plurality of anchor loop strand portions or looped strands 142(1)-142(4), which, as further explained below, is the portion of the eyelet system 140 that extends outwardly from the area between the top surface 132 of the sole structure 130 and the upper 120 to form a series of eyelet loops. While the example embodiment depicts four looped strands 142(1)-142(4), it is noted that any selected number of looped strands may be provided (e.g., one looped strand, two looped strands, etc.) depending upon a particular application. As further illustrated in FIG. 1, a fastening element 150 (e.g., shoe lace) may be threaded through the looped strands 142(1)-142(4) of the eyelet system 140 such that the fastening element 150 extends across at least a portion of the midfoot region 112 of the upper 120 (i.e., from the lateral side 100 to the medial side 300). With the looped strands 142(1)-142(4) extending outwardly from between the upper 120 and the top surface 132 of the sole structure 130, the looped strands 142(1)-142(4) are configured to receive the fastening element 150. While FIG. 1 only illustrates that the eyelet system 140 and the looped strands 142(1)-142(4) are disposed on the lateral side 100 of the article of footwear 10, the fastening element 150 may be further threaded through a second eyelet system (not illustrated) disposed on the medial side 300 of the article of footwear 10. In one embodiment, the second eyelet system may be similar to eyelet system 140, where the second eyelet system extends outwardly from an area between the coupling of the upper 120 to the top surface 132 of the sole structure 130, but on the medial side 300 of the article of footwear 10. In another embodiment, however, the second eyelet system may be a more conventional eyelet system, where the second eyelet system is a series of openings disposed within the midfoot region of the upper 120 on the medial side 300. The fastening element 150 may be utilized to secure or tighten the upper 120 around the foot disposed within the interior of the upper 120.

Figure 2A:
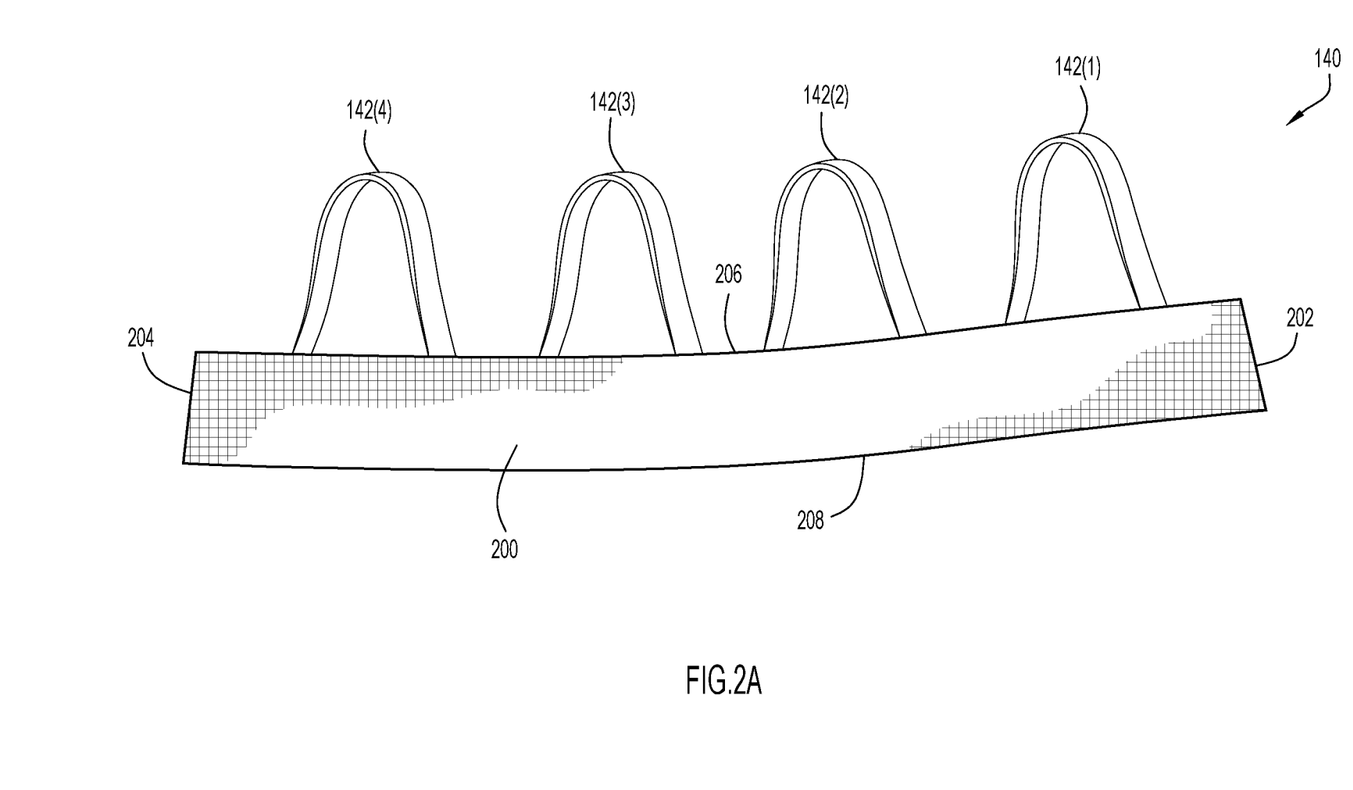
FIG. 2A illustrates a top view of an eyelet system of the embodiment of the article of footwear illustrated in FIG. 1.

The eyelet system 140, as illustrated in FIG. 2A, includes looped strands 142(1)-142(4) that are attached to a tertiary anchor member or base structure 200. The base structure 200 may be elongated with a distal end 202, an opposite proximal end 204, a first elongated edge 206 spanning between the distal and proximal ends 202, 204, and a second elongated edge 208 also spanning between the distal and proximal ends 202, 204 opposite of the first elongated edge 206. The looped strands 142(1)-142(4) extend from the first elongated edge 206 of the base structure. As illustrated in FIG. 2A, the base structure 200 may be constructed from a textile or fabric material. In other embodiments, the base structure 200 may be constructed from any conventional material, including, but not limited to, plastics, metal, etc.

Figure 2B:
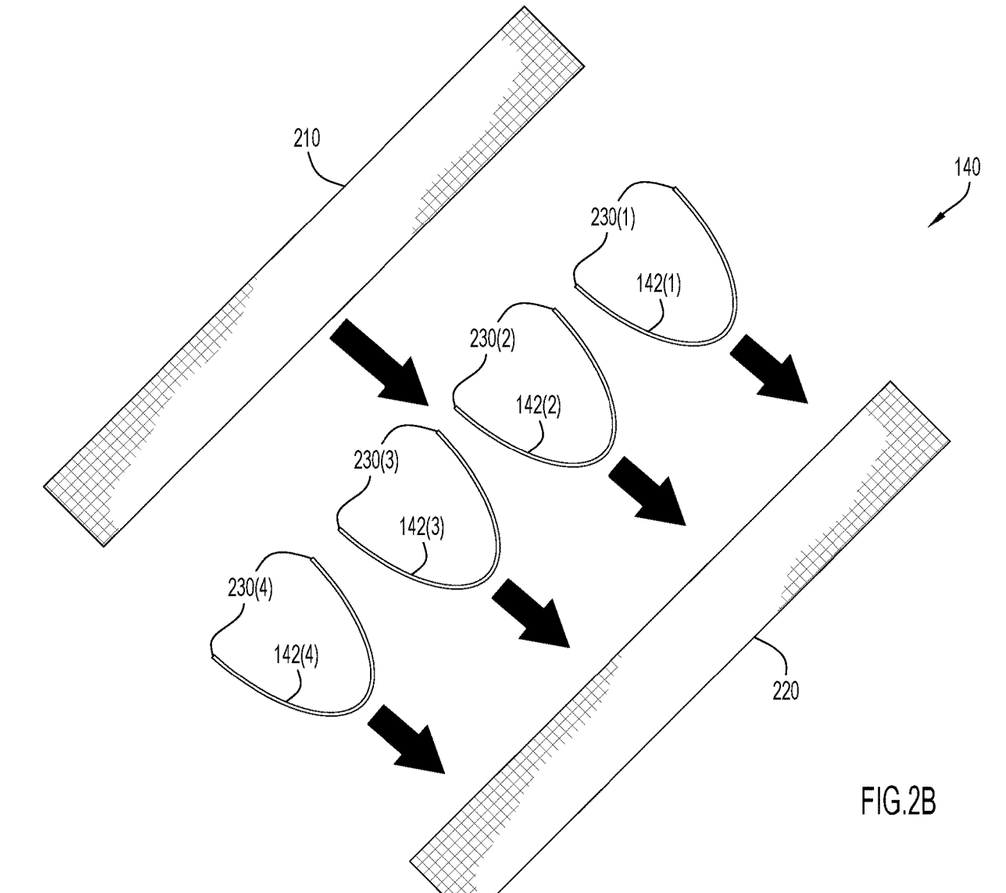
FIG. 2B illustrates a schematic exploded view of the eyelet system illustrated in FIG. 2A.

As illustrated in FIG. 2B, the base structure 200 may be constructed from a top layer 210 and a bottom layer 220. Furthermore, each of the looped strands 142(1)-142(4) includes a pair of ends 230(1)-230(4), respectively. The pair of ends 230(1)-230(4) of each of the looped strands 142(1)-142(4) may be disposed between the top layer 210 and the bottom layer 220 of the base structure 200, where the top layer 210 of the base structure 200 and the bottom layer 220 of the base structure 200 are adhered together. The top layer 210 and the bottom layer 220 of the base structure 200 may be adhered via any conventional means, including, but not limited to, stitching, bonding, adhesives, etc. Thus, the pair of ends 230(1)-230(4) of each of the looped strands 142(1)-142(4) may be disposed between the top and bottom layers 210, 220 of the base structure 200 (i.e., sandwiched between the layers 210, 220) to secure the looped strands 142(1)-142(4) to the base structure 200. Fixing the looped strands 142(1)-142(4) between the top layer 210 and the bottom layer 220 enables the looped strands 142(1)-142(4) to be more securely coupled to the base structure 200 than simply coupling the looped strands 142(1)-142(4) to the top or bottom surface of the base structure 200. In addition, the base structure 200 can comprise a plurality of separate layers that are secured together (such as top layer 210 and bottom layer 220 as shown in FIG. 2B). Alternatively, the base structure 200 can include a single layer (or multi-layered) sheet that is folded over upon itself (e.g., forming a "U" shape with the ends 230 of the looped strands 142(1)-142(4) secured within the folded structure) so as to define top and bottom portions of the base structure 200 that are connected or continuous with each other along one side of the base structure 200.

In an alternative embodiment, the plurality of looped strands 142 extending from the base structure 200 can be defined by a single continuous strand that extends in a zig zag or undulating (e.g., sinusoidal) pattern, where portions of the strand attach with portions of the base structure 200 while other portions of the strand extend from the base structure (thus forming the loops 142(1)-142(4)). Alternatively, two or more looped strands 142 can be formed from a single, continuous strand while any other one or more looped strands 142 can be defined by at least another single, continuous strand (i.e., the looped strands 142(1)-142(4) are not defined by a single, continuous strand but instead comprise two or more separate strands).

Each of the looped strands 142(1)-142(4) may be constructed from a flexible textile or fabric material. Each of the looped strands 142(1)-142(4) is flexible, possessing tensile strength sufficient for its described purpose (to capture a fastening element and secure a shoe to a user's foot). The term "strand" as used herein includes a single fiber or filament as well as an ordered assemblage of textile fibers having a high ratio of length to diameter and combined to form a single unit such as a yarn, a cord, a braid, a rope, a bundle, etc. In an example embodiment, a strand is a yarn that includes one or a plurality of fibers (where a plurality of fibers can be twisted together or combined in any other suitable manner to form a single unit as described herein). By way of specific example, each of the looped strands 142(1)-142(4) may be may be a nylon cord, a polyester cord, or a cord formed of a polyolefin (e.g., polyethylene). In still other embodiments, the strand comprises a cable formed of, e.g., plastic or metal such as steel.

For the embodiment illustrated in FIGS. 1, 3A, and 3B, the base structure 200 of the eyelet system 140 is secured to the top surface 132 of the sole structure 130. In the embodiment illustrated in FIGS. 3A and 3B, the sole structure 130 includes a recession or depression 330 that is disposed in the midfoot region 112 of the top surface 132 of the sole structure 130 proximate to the lateral edge 310 of the sole structure 130. While the embodiment of the sole structure 130 illustrated in FIGS. 3A and 3B illustrates only one recession 330, other embodiments of the sole structure 130 may include any number of recessions located along any portion or part of the sole structure 130.

As illustrated in FIGS. 3A and 3B, the eyelet system 140 is coupled to the top surface 132 of the sole structure 130, where the base structure 200 of the eyelet system 140 is disposed within the recession 330. More specifically, the base structure 200 is disposed within the recession 300 such that the first elongated edge 206 of the base structure 200 is aligned with the lateral edge 310 of the sole structure 10. While not illustrated, the bottom layer 220 of the base structure 200 of the eyelet system 140 is coupled to the top surface 132 of the sole structure 130. In addition, when coupled to the sole structure 130, the looped strands 142(1)-142(4) are configured to at least partially extend outwardly from the lateral edge 310 of the sole structure 130. Furthermore, the recession 330 is shaped and sized such that, when the eyelet system 140 is disposed within the recession 330, the top layer 210 of the base structure 200 of the eyelet system 140 is aligned, and sits flush, with the top surface 132 of the sole structure 130. Thus, the recession 330 enables the eyelet system 140 to be coupled to the top surface 132 of the sole structure 130 without causing irritation or discomfort on the bottom surface of a foot disposed within the upper 120 of the article of footwear 10. In other words, the recession 330 allows the top layer 210 to align with the top surface 132 of the sole structure 130 such that a user of the article of footwear cannot feel where the base structure 200 is secured to the top surface 132 of the sole structure 130 (i.e., the base structure 200 of the eyelet system 140 and the top surface 132 of the sole structure 130 feels like a continuous surface to the bottom of the foot of the user of the article of footwear 10).

While the embodiment of the eyelet system 140 illustrated in FIGS. 1, 3A, and 3B, is coupled and secured to the top surface 132 of the sole structure 130 such that the eyelet system 140 is secured to the article of footwear 10 between the top side 132 of the sole structure 130 and the upper 120, in other embodiments, the eyelet system 140 may be coupled to the article of footwear 10 at a variety of other locations. For example, the eyelet system 140, and more specifically, the base structure 200 of the eyelet system 140, may be coupled and secured to the bottom surface of the upper 120 and/or a strobel portion that is secured to the upper 120. In another example, the base structure 200 of the eyelet system 140 may be coupled and secured to the exterior surface of the upper 120. Furthermore, in yet another example, the base structure 200 of the eyelet system 140 may be coupled to an interior surface portion of the upper 120 (e.g., within the cavity formed by the upper 120), where the upper 120 is configured to enable the looped strands 142(1)-142(4) to extend through the upper 120 such that the looped strands 142(1)-142(4) are primarily located on the exterior side of the upper 120. In a further embodiment, where the upper 120 is constructed of multiple layers (e.g., multiple knit or woven layers), the base structure 200 of the eyelet system 140 may be coupled and secured between an exterior layer and an interior layer of the upper 120, where the looped strands 142(1)-142(4) extend through at least a portion of the layers of the upper 120 and are primarily located on the exterior side of the upper 120.

Because the looped strands 142(1)-142(4) of the eyelet system 140 are constructed of flexible strands, the loops formed by the strands 142(1)-142(4) are able to adjust to the topography of the foot disposed within the upper 120 of the article of footwear 10 to position the fastening element 150 in a comfortable position that conforms to the shape of the foot disposed within the upper 120. During operation, as a user/wearer of the article of footwear 10 pulls on the fastening element 150, the fastening element 150 is pulled through the loops formed by the looped strands 142(1)-142(4). The continued pulling of the fastening element 150 causes the looped strands 142(1)-142(4) to move or transition along the lateral side and/or medial side of the upper 120 of the article of footwear 10. This causes the combination of the fastening element 150 and the looped strands 142(1)-142(4) to conform to the shape or topography of the foot placed within the article of footwear 10. Because the combination of the fastening element 150 and the looped strands 142(1)-142(4) are disposed over the upper 100 proximate to the midfoot region 112 of the article of footwear 10, the pulling of the fastening element 150 also causes the combination of the fastening element 150 and the looped strands 142(1)-142(4) to force the upper 120 to conform and contour to the shape or topography of the foot placed within the article of footwear 10. In addition, when the base structure 200 is coupled to the sole structure 130, as the fastening element 150 is pulled through the looped strands 142(1)-142(4), stress is not imparted onto the upper 120. This reduces the change of tearing/ripping or unwanted bunching of the upper 120, especially when the upper 120 is a tongue-less upper constructed from a knit or woven fabric, as illustrated. This improves the life of the upper 120 while increasing the comfort of the article of footwear 10 (e.g., reducing the creation of pressure points from bundled or bunched portions of the upper).

It is to be understood that terms such as "left," "right," "top," "bottom," "front," "rear," "side," "height," "length," "width," "upper," "lower," "interior," "exterior," "inner," "outer" and the like as may be used herein, merely describe points or portions of reference and do not limit the present invention to any particular orientation or configuration. Further, the term "exemplary" is used herein to describe an example or illustration. Any embodiment described herein as exemplary is not to be construed as a preferred or advantageous embodiment, but rather as one example or illustration of a possible embodiment of the invention.

Although the disclosed inventions are illustrated and described herein as embodied in one or more specific examples, it is nevertheless not intended to be limited to the details shown, since various modifications and structural changes may be made therein without departing from the scope of the inventions and within the scope and range of equivalents of the claims. In addition, various features from one of the embodiments may be incorporated into another of the embodiments. Accordingly, it is appropriate that the appended claims be construed broadly and in a manner consistent with the scope of the disclosure as set forth in the following claims.

What is claimed is:

1. An article of footwear comprising:
    an upper defining a cavity;
    a sole structure coupled to the upper, the sole structure including a top surface and an opposite bottom surface; and
    an eyelet system coupled to the top surface of the sole structure, the eyelet system comprising:
        a base structure disposed on the top surface of the sole structure, the base structure including a top layer and a bottom layer coupled to the top layer, and
        a plurality of loop strand portions coupled to and extending from the base structure, wherein the plurality of loop strand portions are at least partially disposed between the top layer and the bottom layer.

2. The article of footwear according to claim 1, wherein the sole structure further includes a medial side and a lateral side.

3. The article of footwear according to claim 2, wherein the top surface of the sole structure further comprises:

a recess disposed proximate to the lateral side.

4. The article of footwear according to claim 3, wherein the base structure is disposed within the recess of the top surface of the lateral side.

5. The article of footwear according to claim 4, wherein the plurality of loop strand portions extend outwardly from the lateral side of the sole structure.

6. The article of footwear according to claim 1, wherein each loop strand portion comprises a strand with two ends, and the ends of each of the plurality of loop strand portions are coupled to the base structure between the top layer and the bottom layer.

7. The article of footwear according to claim 1, wherein at least two loop strand portions are defined along a single, continuous strand, and the single, continuous strand includes other portions that are coupled to the base structure between the top layer and the bottom layer.

8. The article of footwear according to claim 1, further comprising a fastening element threaded through the plurality of loop strand portions.

9. The article of footwear according to claim 1, wherein the base structure of the eyelet system is constructed from a fabric material.

10. An article of footwear comprising:
    an upper defining a cavity;
    a sole structure coupled to the upper; and
    an eyelet system coupled to the sole structure, the eyelet system comprising:
        a base structure coupled to the sole structure such that the base structure is disposed between the upper and the sole structure, the base structure including a top layer and a bottom layer coupled to the top layer, and
        a plurality of loop strands coupled to the base structure, the plurality of loop strands are at least partially disposed between the top layer and the bottom layer and extend outwardly from between the upper and the sole structure.

11. The article of footwear of claim 10, wherein the sole structure further comprises:
    a top surface;
    a bottom surface;
    a medial side;
    a lateral side; and
    a recess disposed in the top surface proximate to the lateral side, the recess and the lateral side intersecting one another to form a lateral edge disposed at least partially along the lateral side.

12. The article of footwear of claim 11, wherein the base structure further comprises:
    a first elongate edge and a second elongate edge, wherein the plurality of loop strands extend from the first elongate edge.

13. The article of footwear of claim 12, wherein the eyelet system is disposed within recess of the sole structure such that the first elongate edge of the base structure is aligned with the lateral edge of the sole structure.

14. The article of footwear of claim 10, wherein the upper is a tongue-less upper constructed from a knit material.

15. The article of footwear according to claim 10, the base structure of the eyelet system is constructed from a fabric material.

* * * * *

UNITED STATES PATENT AND TRADEMARK OFFICE
CERTIFICATE OF CORRECTION

Page 1 of 1

PATENT NO. : 11,350,702 B2
APPLICATION NO. : 16/595742
DATED : June 7, 2022
INVENTOR(S) : Nicole Doenges It is certified that error appears in the above-identified patent and that said Letters Patent is hereby corrected as shown below:

On the Title Page

Item (60) under Related U.S. Application Data:
Please change "Provisional application No. 62/478,866, filed on Mar. 30, 2017." to --Provisional application No. 62/478,868, filed on Mar. 30, 2017.--

Signed and Sealed this
Thirteenth Day of September, 2022

Katherine Kelly Vidal
*Director of the United States Patent and Trademark Office*